United States Patent [19]

Caccia et al.

[11] Patent Number: 4,927,849
[45] Date of Patent: May 22, 1990

[54] SULFONAMIDO DERIVATIVES INHIBITING THE ALDOSE REDUCTASE ENZYME SYSTEM AND PHARMACEUTICAL COMPOSITIONS CONTAINING THEM

[75] Inventors: Giulio Caccia, Viareggio; Massimo Baldacci, Pisa, both of Italy

[73] Assignee: Laboratori Baldacci SpA, Pisa, Italy

[21] Appl. No.: 245,165

[22] Filed: Sep. 16, 1988

[30] Foreign Application Priority Data

Sep. 16, 1987 [IT] Italy ................. 21930 A/87

[51] Int. Cl.$^5$ ............ A61K 31/35; C07D 311/86
[52] U.S. Cl. .................... 514/455; 549/392; 549/393
[58] Field of Search ............. 549/392, 393; 514/455

[56] References Cited

U.S. PATENT DOCUMENTS 3,678,077  7/1972  Nakanishi et al. ............... 549/392
3,849,565  11/1974  Pfister et al. ................... 549/393

Primary Examiner—Nicky Chan
Attorney, Agent, or Firm—Cushman, Darby & Cushman

[57] ABSTRACT

The xanthosulfonamido and benzensulfonamido derivatives corresponding to the formula:

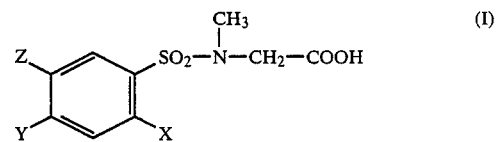

wherein x represents hydrogen, alkyl, alkoxy or halogen, Y represents an alkyl, alkoxy or halogen and Z represents the group

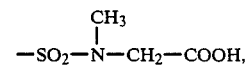

or Y and Z taken together form the group:

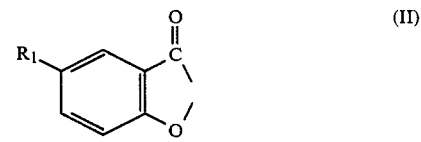

wherein $R_1$ in turn is a group selected among electron attracting groups, halogens and the group:

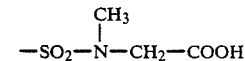

itself, possess activity in inhibiting the aldose-reductase enzyme system and are thus useful in the treatment of the complications, at the eye and peripheral neuropathy levels, as induced by diabetes.

7 Claims, No Drawings

SULFONAMIDO DERIVATIVES INHIBITING THE ALDOSE REDUCTASE ENZYME SYSTEM AND PHARMACEUTICAL COMPOSITIONS CONTAINING THEM

The present invention relates to novel sulfonamido derivatives having the property of inhibiting the aldose reductase enzyme system, particularly, xanthosulfonamido and benzensulfonamido derivatives.

In recent years a number of studies has been carried out with respect to the diabetes and mainly to the complications induced by this disease, such as cataract, retinitis and peripheral neuropathy.

According to these studies, particularly, the genesis of those complications seems to be attributed to the enzyme catalyzing the conversion of glucose into sorbitol and of galactose into dulcitol.

As a matter of fact, under pathological conditions, the excess of glucose present in the diabetic patient causes an accumulation of intracellular sorbitol to occur with relevant hyperosmotic effect and inflow of the fluids within the cell.

This picture is the pathogenetic base of the above mentioned complication of the diabetes, mainly of those relating to eyes and to the peripheral neuropathy.

Referring to this pathogenetic origin substances have investigated capable of inhibiting the aldose reductase enzyme.

For information purpose the following papers published in the literature can be cited:

N. Canal and G. Comi, Aldose Reductase Inhibitors: Pharmacological data and therapeutic perspectives, TIPS- Aug. 1985, pag. 328;

Cristopher A. Lipinski et al., Aldose Reductase Inhibitors as a New Approach to the Treatment of Diabetic Complications, Ann. Rep. Med. Chem., 19, 169; 1984;

Richard Poulson et al, Inhibition of Aldose Reductase in Five Tissues of the Streptozotocin Diabetic Rat, Biochem. Pharmacol. 32, 1495, 1983;

D. Dvornik et al, Polyol Accumulation in Galactosemic and Diabetic Rats: Control by an Aldose reductase Inhibitor, Science, 182, 1146, 1973;

N. Simard-Duquesne et al., Prevention of Cataract Development in Severely Galactosemic Rats by the Aldose Reductase Inhibitor, Tolrestat (42048), Pr. Soc. Exp. Biol. Med., 178, 599, 1985;

Sorbinil, Aldose Reductase Inhibitor, Drug of the Future, 11 (4), 345, 1986.

From this literature it is evident that the relationship between the complications of the diabetes and aldose reductase enzyme system became more and more precise and that the inhibition of the latter system is considered a main route for the therapeutical treatment of these complications.

The subject of the present invention are novel compounds of the class of the sulfonamido derivatives, particularly xanthosulfonamido derivatives and benzensulfonamido derivatives, showing a remarkable inhibiting activity towards the aldose reductase enzyme system, whereby they appear as useful therapeutic agents in the treatment of the above mentioned diabetes complications.

The novel derivatives according to the present invention have the following general formula:

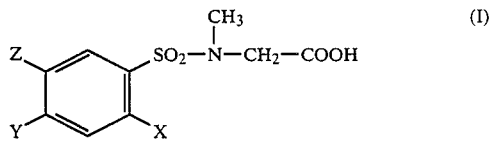

wherein X and Y represents an alkyl, alkoxy or halogen and Z represents the group

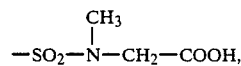

or Y and Z taken together form the group:

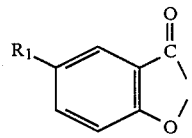

wherein $R_1$ in turn is a group selected among the electronattracting groups, halogens and the group

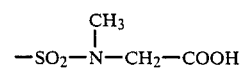

itself.

As the preferred examples of electronattracting groups there can be cited —COOH, —CO—CH$_2$—R$_2$, CF$_3$ (wherein R$_2$ is an alkyl radical), whereas as regards the halogens, the selection can take place among fluorine, chlorine and bromine.

The process for the preparation of the compounds of the present invention contemplates in a first step the preparation of the sulfo-chloride, having the desired substituents, and, in a second step, the reaction of the sulfo-chloride with N-methylglycine.

The following examples illustrate, without limiting purpose, the preparation of the compounds of the present invention.

EXAMPLE 1

(a) 80 g (0.347 moles) of 2-chloroxanthone (DHAR, J. Chem. Soc. 117, 1068) are suspended in 210 ml of chlorosulfonic acid (368.1 g; 3.16 moles) in a 500 ml one neck flask provided with refluxing coolant and calcium chloride valve. The mixture is slowly heated in an oil bath up to 120° C. under magnetic stirring. It is maintained at 120°-130° C. until the gas development ceases (2-3 h). The cool reaction mixture is carefully dropwise added to a becker containing ground ice under mechanical stirring. A heavy crystalline product is separated which is filtered on Buchner and washed with iced H$_2$O. It is dried in air. There are obtained 112 g (98%) of raw 2-(chlorosulfonyl-7-chloroxanthone. After TLC monitoring (silica gel F$_{245}$; toluene, acetic acid 14:1, visualizer UV) the product is used as such for the next reaction.

(b) The above raw sulfochloride (112 g, 0.340 moles) is suspended in an N-methylglycine solution (151.3 g; 1.7 moles) in 1N KOH (1.7 liters). The suspension is slowly heated with a water bath under magnetic stirring. At about 70° C. all the solid goes into solution leaving only a slight cloudyness. The hot solution is filtered on paper and slowly dropwise added to 5N HCl under mechanical stirring.

A white crystalline solid is thus separated. The product is cooled under stirring. The raw product is filtered on Buchner, washed with H₂O and dried. After crystallization from acetic acid there are obtained 94 g (72.4%) of 7-chloro-2-N-methyl-N-carboxymethyl)sulfamoylxanthone, m.p. 246°–248° C. TLC: one spot (silica gel F$_{254}$; toluene, dioxane, formic acid 8:3:1).

NMR (60 MHZ; solvent Polysol; δTMS=O) δ2.95, S, 3H,

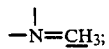

4.05, S, 2H,

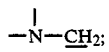

7.57 - 8, 70, m, 6H aromatics.
Analysis for C$_{16}$H$_{12}$Cl N O$_6$S: M.P. 381.5.

|  | C | H | N | Cl | S |
| --- | --- | --- | --- | --- | --- |
| Calc. % | 50.32 | 3.14 | 3.66 | 9.30 | 8.38 |
| Found % | 50.62 | 3.09 | 3.57 | 9.63 | 8.25 |

EXAMPLE 2

Starting from 2-fluoroxanthone (F. L. Allen and Coll., Tetrahedron 6, 315, 1959) and proceeding as described in example 1, there is obtained with a total yield of 75% the 7-fluoro-2-(N-methyl-N-carboxymethyl)sulfamoylxanthone. TLC: one spot.
m.p. 233.5°–235° C. (acetic acid).
NMR: δ3.95, S, 3H,

4.05, 2H,

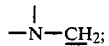

7.6–8.7, m, 6H aromatics.
Analysis for C$_{16}$H$_{12}$FNO$_6$S: M.P. 365.

|  | C | H | N | S |
| --- | --- | --- | --- | --- |
| Calc. % | 52.60 | 3.28 | 3.83 | 8.76 |
| Found % | 52.45 | 3.21 | 3.75 | 8.70 |

EXAMPLE 3

11.8 g (30 mmoles) of xanthone-2,7-disulfochloride (H. Ulrich, U.S. Pat. No. 3,714,194 (1973); C.A. 78, 136074 U) are added to a solution of methyl-glycine (26.7 g; 300 mmoles) in 150 ml of 2N NaOH, under magnetic stirring. The suspended solid is quickly dissolved. After storage for one night, the solution is filtered on paper and dropwise added to 5N HCl under stirring. A white microcrystalline product is separated; the suspension is then centrifugated at 3000 rpm for 10–15 minutes. The mother solution is removed by decantation and the solid is washed with H₂O still by centrifugation.

The product is taken with isopropanol and filtered on Buchner. The dried raw product is crystallized from DMF/isopropanol; there are thus obtained 7g (46.8%) of 2,7-bis(N-methyl-N-carboxymethyl)sulfamoylxanthone having m.p.>250° C. TLC (silica gel F 254; n-butanol, H₂O acetic acid 4:1:2:; UV detector): one spot.

NMR δ2.95, s, 6H,

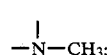

4.08, 4H,

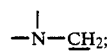

7.7–8.8, m, 6H aromatics.
Analysis for C$_{19}$H$_{18}$N$_2$O$_{10}$S$_2$M.P. 498 (neutralization equivalent weight 498).

|  | C | H | N | S |
| --- | --- | --- | --- | --- |
| Calc. % | 45.78 | 3.61 | 5.62 | 12.85 |
| Found % | 45.60 | 3.51 | 5.45 | 12.80 |

EXAMPLE 4

42 g (0.138 moles) of 4,6-dimethylbenzen-1,3-disulfochloride (Pollack, Lusting, Annalen, 433, 193) are added in portions under magnetic stirring to a solution of N-methylglycine (50 g; 0.560 moles) in 420 ml of 2N, NaOH, externally cooling at 0°–5° C.

The solid is slowly dissolved; after 12 hours at room temperature the solution is filtered on paper and dropwise added to iced 5N HCl under stirring. A white product is separated which is filtered on Buchner and washed with H₂O.

It is crystallized from ethanol/H₂O giving 41g (73.2%) of 4,6-dimethyl-1,3-bis (N-methyl-N-caboxymethl) sulfamoylbenzene, m.p. 189°–190° C. TLC (toluene, dioxane, formic acid, 5:5:1): one spot (UV).
Analysis for C$_{14}$H$_{20}$N$_2$O$_8$S$_2$, M.P. 408 (neutralization equimolar weight=408).

|  | C | H | N | S |
| --- | --- | --- | --- | --- |
| Calc. % | 41.17 | 4.90 | 6.86 | 15.68 |
| Found % | 41.05 | 4.85 | 6.70 | 15.55 |

The compounds of the present invention have been subjected to pharmacological and toxicity tests with the hereinafter stated conditions.

For sake of semplicity the tested compounds are indicated by abbreviations in the following manner:
Compound of the example 4: ARI 1
Compound of the example 1: ARI 6
Compound of the example 2: ARI 8
Compound of the example 3: ARI 9
The toxicity tests after only one administration have been carried out on two animal species (mice and rats), using two administration routes (os, iv).

(a) Acute toxicity: mice

For these tests Swiss mice have been used, of both sexes, having average weight 20 g, fasted after 18 hours and administered with water ad libitum. The animals were maintained under standard environment conditions (temperature: 20°-22° C. and moisture 50%).

The compounds have been administered by gastric probe, suspended in Methocell or by injection (iv) dissolved in physiological solution with the addition of sodium bicarbonate.

The animals have been kept under observation for 15 days.

The controls have been carried out several times in the first days and twice a day in the next days. In the table 1 the conditions used and the results obtained are reported.

(b) Acute toxicity: rat

Wistar rats, of both sexes have been used of average weight of 120 g, fasted after 18 hours and with water at libitum. The conditions of stalling and the administration ways were the same as those reported in the preceeding paragraph (acute toxicity: mouse).

In the table II the obtained results are reported.

TABLE 1

| Species | Drug | Dose and administration route | Administration volume | N. of animal used per group | % Death |
|---|---|---|---|---|---|
| MOUSE (Swiss) | ARI 1 | 5000 mg/kg/os | 20 ml/kg | 5 ♂ + 5 ♀ | 0 |
| | ARI 8 | 5000 mg/kg/os | | 5 ♂ + 5 ♀ | 10 |
| | ARI 1 | 500 mg/kg/iv | 20 ml/kg | 5 ♂ + 5 ♀ | 0 |
| | ARI 8 | 400 mg/kg/iv | | 5 ♂ + 5 ♀ | 0 |

TABLE 2

| Species | Drug | Dose and administration route | Administration volume | N. of animal used per group | % Death |
|---|---|---|---|---|---|
| RAT (Wistar) | ARI 1 | 5000 mg/kg/os | 20 ml/kg | 5 ♂ + 5 ♀ | 0 |
| | ARI 8 | 5000 mg/kg/os | 20 ml/kg | 5 ♂ + 5 ♀ | 30 |
| | ARI 1 | 500 mg/kg/iv | 20 ml/kg | 5 ♂ + 5 ♀ | 0 |
| | ARI 8 | 500 mg/kg/iv | 20 ml/kg | 5 ♂ + 5 ♀ | 40 |
| | ARI 8 | 400 | 20 ml/kg | 5 ♂ + 5 ♀ | 0 |

TOXICOLOGY OF THE COMPOUND ARI 6
(Example 1)

| | |
|---|---|
| 1. Acute toxicity in the rat ip | 1000 mg/kg |
| 2. Acute toxicity in the rat per os | 1000 mg/kg |
| 3. Acute toxicity in the mouse per os | 1000 mg/kg |
| 4. Acute toxicity in the mouse ip | 1000 mg/kg |

Toxicity per oral administration repeated in the rat (30 days) -Test protocol:

| Compound | Doses mg/kg/die |
|---|---|
| Controls | — |
| ARI 6 | 100 |
| ARI 6 | 200 |
| ARI 6 | 300 |

Results:
No death
Behaviour and general status (no variation with respect to the control group).
Biochemical and hematological parameters (no significant variation with respect to the controls).
Microscope and hystomorphological examination: no alteration.

"In vitro" pharmacological tests.

"In vitro" tests have been carried out to evaluate the inhibition of the aldose reductase activity, prepared from the extract of bovine crystalline lenses.

Preparation of the raw extracts.

4 bovine crystalline lenses (8 g) are homogenized by means of Potter in ice bath with 40 ml of 50 mM phosphate buffer, pH 6.8, containing 2-mercaptoethanol pH (5 nM). After centrifugation (12.000×g -20 min-4° C.) the supernatent is brought to 40% saturation with an ammonium sulphate and centrifugated again (14.000×g). The supernatent is then brought to the 80% saturation ($NH_4)_2SO_4$) and, after centrifugation for 20 minutes and at 14.000×g, the sedimented matter is recovered and suspended in 7 ml of phosphate buffer. The enzymatic preparation is dialyzed by ultrafiltration with AMICON ultrafiltration cell.

Dosage of the enzymatic activity

400 μl of phosphate buffer 0.25% pH 6.8 are supplemented with 200 μl of NADPH solution (final concentration 100 μM), 170 μl of ammonium sulphate solution (final concentration 0.4M), 100 μl of glyceraldehyde (5mM), 40 μl of the preparation of the enzymatic extract and phosphate buffer or portions of the several compounds to be tested up to the final volume of 1070 μl.

The reaction is carried out at 37° C., it starting with the addition of the enzyme and the diminution of optical density (D.O.) at 340 nM is monitored by DU6 Beckman spectro photometer programmed for the direct calculation of the reaction rate (ΔE/min.).

The reference cuvette contains all the several substances apart from the substrate.

TABLE 3

$IC_{50}$ (M)* values of the several compound on the aldose reductase activity of raw extracts originating from bovine crystalline lens.

| Compounds | $IC_{50}$ |
|---|---|
| ARI 1 | $3.6 \cdot 10^{-6}$ M |
| ARI 5 | $1.4 \cdot 10^{-6}$ M |
| ARI 6 | $9.2 \cdot 10^{-6}$ M |
| ARI 8 | $1.0 \cdot 10^{-6}$ M |
| ARI 9 | $1.0 \cdot 10^{-6}$ M |
| SORBINIL | $2.0 \cdot 10^{-6}$ M |

*IC = 50 = concentration given in moles capable of inhibiting by 50% the enzymatic activity.

The obtained results shown the certain inhibiting action of the compounds of the invention of the aldose reductase activity.

The compounds ARI 8 and ARI 9, for this experimental model show higher activity, with respect to the of sorbinil and of ARI 1.

"In vivo" pharmacological tests.

With the compound bearing the abbreviation ARI 6 the following tests have been carried out in the rat and in the rabbit.

Action on the appearance of the galactosemic cataract (rat)

Action on the appearance of the diabetic cataract (rat).

Results

In table 4 the experimental results obtained in the rat are reported. It can be pointed out that the appearance of the lenticular cloudiness in the control animals developed in 20 days on average, whereas the treatment with the doses of 5 mg/kg has shown a delay of about 20 days for the appearance of the cataract.

A more intense effect took place with the higher doses. The table 5 shows the effect of the dose of 25 mg/kg on the appearance of the diabetic cataract. In this experimental model too the appearance of the cataract has been observed with a delay of about 30 days with respect to the controls.

TABLE 4

Effects of the administration of ARI-6 (5 and 25 mg/kg/die, os) on the appearance of the galactosemic cataract in the rat.

| Days from the beginning of the diet | PLACEBO (20) | ARI 6 5 mg/kg/die (20) | ARI 6 25 mg/kg/die (20) |
|---|---|---|---|
| 5 | 0.0 | 0.0 | 0.0 |
| 10 | 10.0 | 0.0 | 0.0 |
| 15 | 50.0 | 0.0 | 0.0 |
| 20 | 100.0 | 0.0 | 0.0 |
| 25 | 100.0 | 15.0 | 0.0 |
| 30 | 100.0 | 20.0 | 0.0 |
| 35 | 100.0 | 40.0 | 0.0 |
| 40 | 100.0 | 100.0 | 15.0 |
| 45 | 100.0 | 100.0 | 25.0 |
| 50 | 100.0 | 100.0 | 100.0 |

The values are not expressed as a percentage. In the brackets the number of animals for each group is indicated.
The diet contains D-galactose 50%.

TABLE 5

Effects of the administration of ARI 6 (25 mg/kg/die, per os) on the apperance of the diabetic cataract in the rat.

| Days from the administration of streptozotocine | Placebo (10) | ARI 6 25 mg/kg/die (10) |
|---|---|---|
| 5 | 0.0 | 0.0 |
| 10 | 10.0 | 0.0 |
| 15 | 50.0 | 0.0 |
| 20 | 100.0 | 0.0 |
| 25 | 100.0 | 0.0 |
| 30 | 100.0 | 0.0 |
| 35 | 100.0 | 0.0 |
| 40 | 100.0 | 20.0 |
| 45 | 100.0 | 30.0 |
| 50 | 100.0 | 100.0 |

The values are expressed as percentages. Within brackets there are indicated the animals for each group.

In tables 6 and 7 corresponding to the tables 4 and 5, the values obtained with the compound ARI-1 are reported.

TABLE 6

Effects of the administration of ARI-1 (5 and 25 mg/kg/die, os) on the appearance of the galactosemic cataract in the rat.

| Days from the beginning of the diet | PLACEBO (20) | ARI 1 5 mg/kg/die (20) | ARI 1 25 mg/kg/die (20) |
|---|---|---|---|
| 5 | 0/20 (0.0) | 0/20 (0.0) | 0/20 (0.0) |
| 10 | 8/20 (40.0) | 0/20 (0.0)* | 0/20 (0.0)* |
| 15 | 10/20 (50.0) | 0/20 (0.0)* | 0/20 (0.0)* |
| 20 | 20/20 (100.0) | 0/20 (0.0)* | 0/20 (0.0)* |
| 25 | 20/20 (100.0) | 3/20 (15.0)* | 0/20 (0.0)* |
| 30 | 20/20 (100.0) | 4/20 (20.0)* | 0/20 (0.0)* |
| 35 | 20/20 (100.0) | 8/20 (40.0)* | 0/20 (0.0)* |
| 40 | 20/20 (100.0) | 8/20 (100.0)* | 3/20 (15.0*) |
| 45 | 20/20 (100.0) | 20/20 (100.0)* | 5/20 (25.0*) |
| 50 | 20/20 (100.0) | 20/20 (100.0) | 20/20 (100.0) |

The values represent the number of eyes with cataract on the total number of observed eyes. The percentage values are put between brackets.
*Significant difference with respect to the controls (p < 0.05, Fischer Test).

TABLE 7

Effects of the administration of ARI-1 (25 mg/kg/die, per os) on the appearance of the diabetic cataract in the rat.

| Days from the streptozotocine administration | PLACEBO | ARI 1 25 mg/kg/die |
|---|---|---|
| 5 | 0/20 (0.0) | 0/20 (0.0) |
| 10 | 8/20 (40.0) | 0/20 (0.0)* |
| 15 | 10/20 (50.0) | 0/20 (0.0)* |
| 20 | 20/20 (100.0) | 0/20 (0.0)* |
| 25 | 20/20 (100.0) | 0/20 (0.0)* |
| 30 | 20/20 (100.0) | 0/20 (0.0)* |
| 35 | 20/20 (100.0) | 0/20 (0.0)* |
| 40 | 20/20 (100.0) | 4/20 (20.0)* |
| 45 | 20/20 (100.0) | 6/20 (30.0)* |
| 50 | 20/20 (100.0) | 20/20 (100.0)* |

The values represent the number of eyes with cataract with respect to the total number of observed eyes. The percentage values are put in brackets.
*Significant difference with respect to the controls. (p < 0.05, Fischer Test).

The pharmaceutical compositions according to the invention, namely including the novel sulfonamido derivatives as the active ingredient, and useful for the prevention and/or therapy of retinic damages (cataract, retinopathy etc.) and of peripheral neuropathies in diabetic patients. The pharmaceutical compositions of the invention are in form of a tablets or capsules, containing the standard vehicles and excipients, besides the active compounds, and prepared according to the well known pharmaceutical technologies. The daily posology foreseen for the compositions of the present is of 50 to 200 mg/day, depending on the seriousness of the disease.

Consequently the tablets or capsules shall contain from 5 to 200 mg of active compound. Depending on the solubility in water of the active compounds also solutions for parenteral administration are provided.

What is claimed is:

1. A sulfonamido derivative having the general formula:

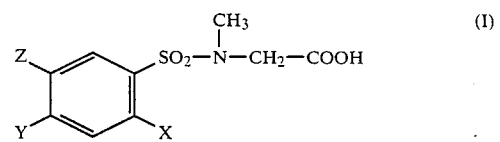

(I)

wherein X represents hydrogen, alkyl, alkoxy or halogen and Y and Z taken together form the group:

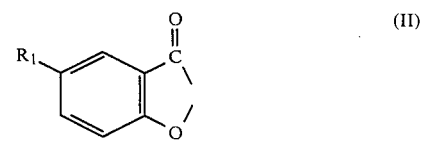

(II)

wherein $R_1$ is a halogen,

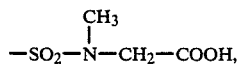

—COOH, —CO—CH$_2$—R$_2$ (where R$_2$ is an alkyl radical) or CF$_3$.

2. The sulfonamido derivative according to claim 1 wherein when R$_1$ is a halogen, said halogen is selected from the group consisting of fluorine, chlorine and bromine.

3. The compound 7-chloro-2-(N-methyl-N-carboxymethyl)-sulfamoylxanthone.

4. The compound 7-fluoro-2-(N-methyl-N-carboxymethyl)-sulfamoylxanthone.

5. The compound 2,7-bis(N-methyl-N-carboxymethyl)-sulfamoylxanthone.

6. A pharmaceutical composition suitable for use in treating retinic damage in a diabetic patient comprising as an active ingredient an amount of said sulfonamido derivative according to claim 1 sufficient to inhibit retinic damage, together with a pharmaceutically acceptable carrier.

7. A method of treating retinic damage in a diabetic patient comprising administering to said patient an amount of said sulfonamido derivative according to claim 1 sufficient to inhibit said damage.

* * * * *